United States Patent [19]

Seybold et al.

[11] 4,239,894
[45] Dec. 16, 1980

[54] THIAZOLE DERIVATIVES

[75] Inventors: Guenther Seybold, Ludwigshafen; Heinz Eilingsfeld, Frankenthal, both of Fed. Rep. of Germany

[73] Assignee: BASF Aktiengesellschaft, Ludwigshafen, Fed. Rep. of Germany

[21] Appl. No.: 920,638

[22] Filed: Jun. 29, 1978

[30] Foreign Priority Application Data

Jul. 16, 1977 Fed. Rep. of Germany ........... 2732221

[51] Int. Cl.³ .......................................... C07D 277/20
[52] U.S. Cl. .................... 548/194; 548/196; 548/198; 544/111; 546/209
[58] Field of Search ................ 260/306.7 T; 548/196, 548/198, 194; 546/209; 544/111

[56] References Cited

U.S. PATENT DOCUMENTS

| | | | |
|---|---|---|---|
| 3,547,917 | 12/1970 | Kulka et al. | 260/306.8 R |
| 3,904,629 | 9/1975 | Failli et al. | 260/306.8 R |
| 4,018,785 | 4/1977 | Maeda et al. | 260/306.7 T |

*Primary Examiner*—Nicholas S. Rizzo
*Attorney, Agent, or Firm*—Oblon, Fisher, Spivak, McClelland & Maier

[57] ABSTRACT

An organic compound of the general formula

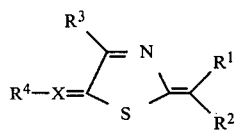

where $R^1$ and $R^2$ are cyano, formyl, substituted or unsubstituted alkanoyl or aroyl, a carboxylic acid ester group, substituted or unsubstituted carbamoyl or sulfamoyl, alkylsulfonyl, arylsulfonyl or alkylsulfinyl, or $R^1$ and $R^2$ together may be a cyclic radical, $R^2$ may also be alkyl, aryl or hetaryl, $R^3$ is hydrogen, substituted or unsubstituted alkyl, aryl or hetaryl, X is CH, $CR^5$ or N, $R^4$ is a radical of the formula

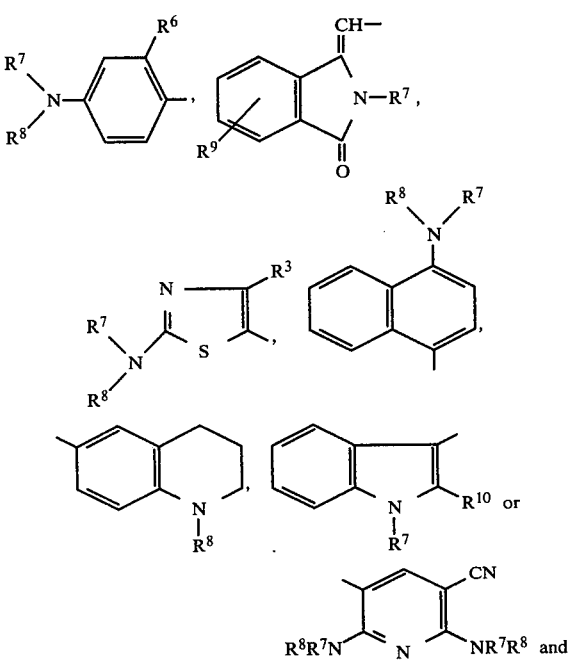

$R^5$ to $R^{10}$ are substituents conventionally present in dyes.

The compounds may be used as dyes for synthetic and natural fibers and give very fast dyeings.

5 Claims, No Drawings

THIAZOLE DERIVATIVES

The present invention relates to a compound of the general formula I

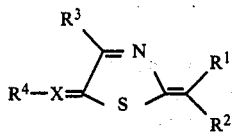

where
- $R^1$ and $R^2$ are cyano, formyl, substituted or unsubstituted alkanoyl or aroyl, a carboxylic acid ester group, substituted or unsubstituted carbamoyl or sulfamoyl, alkylsulfonyl, arylsulfonyl or alkylsulfinyl,
- $R^1$ and $R^2$ together may be a cyclic radical,
- $R^2$ may also be alkyl, aryl or hetaryl,
- $R^3$ is hydrogen, substituted or unsubstituted alkyl, aryl or hetaryl,
- X is CH, $CR^5$ or N, and
- $R^4$ is a radical of the formula

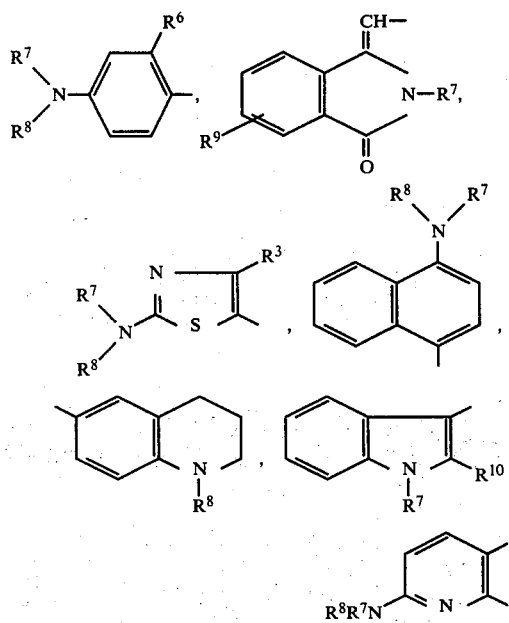

where
- $R^5$ to $R^{10}$ are substituents conventionally present in dyes.

More particularly, the invention relates to a compound where

- $R^5$ is alkyl of 1 to 4 carbon atoms, alkoxycarbonyl (where alkoxy is of 1 to 4 carbon atoms), cyano or substituted or unsubstituted phenyl,
- $R^6$ is hydrogen, chlorine, bromine, methyl, hydroxyl, alkoxy of 1 to 4 carbon atoms, alkanoylamino of 1 to 4 carbon atoms or benzoylamino,
- $R^7$ and $R^8$ independently of one another are hydrogen or alkyl of 1 to 5 carbon atoms which is unsubstituted or substituted by hydroxyl, chlorine, cyano, alkoxy of 1 to 4 carbon atoms, alkanoyloxy of 1 to 4 carbon atoms or alkoxycarbonyl (where alkoxy is of 1 to 4 carbon atoms), or are allyl, cyclohexyl, benzyl, phenylethyl or phenyl,
- $R^9$ is hydrogen, chlorine, bromine or alkyl of 1 to 4 carbon atoms and
- $R^{10}$ is methyl or phenyl.

Specific examples of radicals $R^1$, in addition to those already mentioned, are: $COCH_3$, $COC_2H_5$, $COC_3H_7$, $COCH_2Cl$, $COCHCl_2$, $COC_6H_5$, $COC_6H_4Cl$, $COOCH_3$, $COOC_2H_5$, $COOC_3H_7$, $COOC_4H_9$, $COOC_6H_5$, $COO(CH_2)_3OCH_3$, $COO(CH_2)_3OC_2H_5$, $CONHCH_3$, $CONHC_2H_5$, $CONHC_3H_7$, $CONHC_4H_9$, $CON(CH_3)_2$, $CON(C_2H_5)_2$, $CONH_2$, $CONHC_6H_5$,

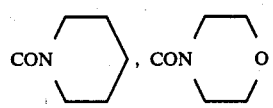

and

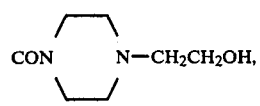

and the corresponding sulfamoyl radicals, $CH_3SO_2$, $C_2H_5SO_2$, $C_4H_9SO_2$ or $CH_3SO$.

$R^2$ may be identical with $R^1$; specific examples of its alternative meanings are: $CH_3$, $C_2H_5$, $C_6H_5$, $C_6H_4Cl$, $CH_3OOC-C_6H_4$, $O_2N-C_6H_4$, $NC-C_6H_4$, $CH_3COC_6H_4$,

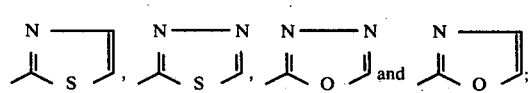

$R^1$ and $R^2$ together may also form a cyclic radical, for example:

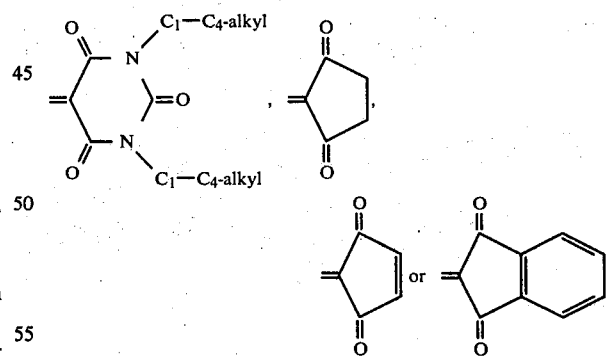

Examples of radicals $R^3$ are: $CH_3$, $C_2H_5$, $C_4H_9$, $C_6H_5$, alkyl—$OC_6H_4$ (where alkyl is of 1 to 4 carbon atoms), $Cl-C_6H_4$, $BrC_6H_4$, alkyl—$S-C_6H_4$ (where alkyl is of 1 to 4 carbon atoms), $H_5C_6S-C_6H_4$ or $CH_2-COO$-alkyl (where alkyl is of 1 to 4 carbon atoms).

Examples of radicals $R^5$ are cyano and $CH_3$, $C_2H_5$, $C_3H_7$, $C_4H_9$, $COOCH_3$, $COOC_2H_5$, $COOC_4H_9$, $C_6H_5$, $C_6H_4Cl$, $C_6H_4Br$, $C_6H_4CH_3$, $C_6H_4OCH_3$, $C_6H_4OC_2H_5$, $C_6H_4SCH_3$, $C_6H_4N(CH_3)_2$ and $C_6H_4N(C_2H_5)_2$.

Specific examples of radicals $R^4$ are radicals derived from aniline, of the formula

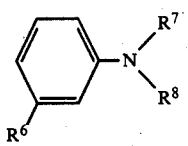

where
R[6] is Cl, CH$_3$, OCH$_3$, OC$_2$H$_5$, OC$_3$H$_7$, NHCOCH$_3$, NHCOC$_2$H$_5$ or NHCOC$_3$H$_7$ and R[7] and R[8] are CH$_3$, C$_2$H$_5$, C$_3$H$_7$, C$_4$H$_9$, C$_2$H$_4$CN, C$_2$H$_4$COO-alkyl (where alkyl is of 1 to 4 carbon atoms), C$_2$H$_4$OH, C$_2$H$_4$O-alkyl (where alkyl is of 1 to 4 carbon atoms) or C$_2$H$_4$OCONH-alkyl (where alkyl is of 1 to 4 carbon atoms).

The compound of the formula I may be prepared by condensing a thiazole of the formula IIa or IIb

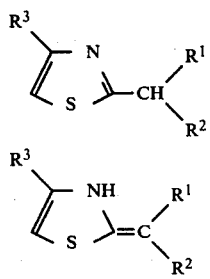

with a compound of the formula III

R[4]—X=O     III where
R[1], R[2], R[3], R[4] and X have the above meanings.

The condensation may be effected by heating the compounds I and II in a solvent—virtually all solvents being suitable—at from 30° to 160° C., preferably from 60° to 100° C. Examples of suitable solvents are methanol, ethanol, propanol, butanol, methylglycol, dioxane, acetone, acetonitrile, DMF, NMP, water, toluene, xylene, chlorobenzene and nitrobenzene.

The condensation is accelerated by adding acid or basic catalysts. The water formed during the reaction can be removed azeotropically from the reaction mixture.

Examples of suitable catalysts are mineral acids, carboxylic acids, eg. formic acid, acetic acid and trichloroacetic acid, phosphorus oxychloride, phosphorus pentachloride, phosphorus trichloride or thionyl chloride.

Examples of basic catalysts are ammonium acetate and amines, eg. piperidine, pyrrolidine, pyridine, triethylamine and triethanolamine.

Details of the method of preparation may be found in the Examples, where parts and percentages are by weight, unless stated otherwise.

The majority of the compounds of the formula IIa and b are new. They may be prepared, for example, by a method similar to that described in German Laid-Open Application DOS No. 1,913,472. Some compounds of the formula IIa and b are described in J. prakt, Chem., 316 (1974), 684.

Compounds of particular industrial importance are those of the formula Ia

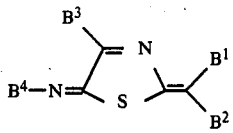

where
B[1] and B[2] are cyano, alkoxycarbonyl (where alkoxy is of 1 to 4 carbon atoms), alkanoyl of 1 to 4 carbon atoms or substituted carbamoyl, B[3] is phenyl which is unsubstituted or substituted by chlorine, bromine, methoxy, ethoxy, methyl or alkylmercapto of 1 to 4 carbon atoms and B[4] is a radical of the formula

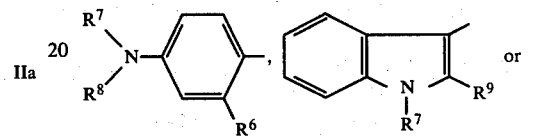

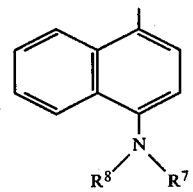

where
R[6] to R[9] have the above meanings; preferred meanings are as follows:

R[6]: hydrogen, NHCOCH$_3$, CH$_3$, OCH$_3$, HNCOC$_2$H$_5$ and Cl.

R[7] and R[8]: hydrogen, CH$_3$, C$_2$H$_5$, CH$_2$—CH=CH$_2$, C$_2$H$_4$CN, C$_2$H$_4$COO-alkyl (where alkyl is of 1 to 4 carbon atoms), C$_6$H$_5$, CH$_2$C$_6$H$_5$ and C$_2$H$_4$OCOCH$_3$.

R[9]: C$_6$H$_5$ and CH$_3$.

The dyes of the formula I are violet to yellowish green and are particularly suitable for dyeing polyester fibers. They give brilliant very fast dyeings; the lightfastness, wetfastness and fastness to heat treatments are to be singled out particularly.

The particular industrial importance of the novel dyes resides in the fact that they may be used to produce green hues on polyester without having to resort to the use of dye mixtures.

The dyes are also suitable for printing polyester/cotton union fabrics, for example by the process described in German Pat. No. 1,811,796.

EXAMPLE 1

21 parts of methyl 4-phenyl-thiazol-2-yl-cyanoacetate, 15 parts of p-nitroso-dimethylaniline hydrochloride, 10 parts of glacial acetic acid and 5 parts of ammonium acetate in 300 parts of toluene are refluxed, the water formed in the reaction being removed. After 4 hours the mixture is cooled and the dye is filtered off.

Yield: 35 parts. Melting point: 246° C. $\lambda_{max}$ in DMF: 655 nm.

The following dyes were prepared by a method similar to that described in Example 1:

| Example | Thiazole component | Carbonal or nitroso compound | Hue on polyester |
|---|---|---|---|
| 2 | 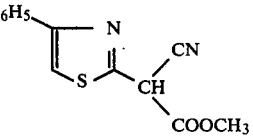 | (CH₃)₂N—⟨⟩—CHO | blue |
| 3 | " |  | reddish blue |
| 4 | " | 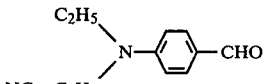 | greenish blue |
| 5 | " | ON—⟨⟩—N(C₂H₅)₂ | greenish blue |
| 6 | " | 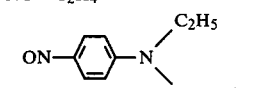 | greenish blue |
| 7 | " | 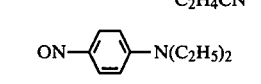 | greenish blue |
| 8 | " | 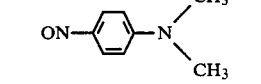 | greenish-blue |
| 9 | " | 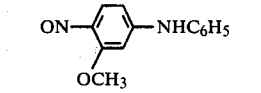 | green |
| 10 | " | 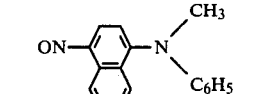 | " |
| 11 | 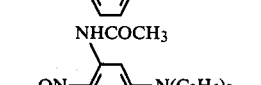 | OCH—⟨⟩—N(CH₃)₂ | blue |
| 12 | " | OCH—⟨⟩—N(C₂H₅)₂ | " |
| 13 | " | 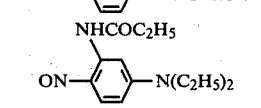 | " |
| 14 | " | 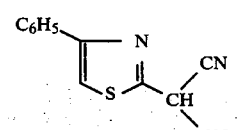 | violet |
| 15 | " | ON—⟨⟩—N(CH₃)₂ | green |
| 16 | " | ON—⟨⟩—N(C₂H₅)₂ | yellowish green |
| 17 | " | 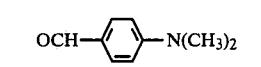 | yellowish green |
| 18 | " | 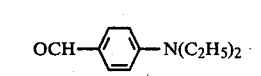 | yellowish green |

| Example | Thiazole component | Carbonal or nitroso compound | Hue on polyester |
|---|---|---|---|
| 19 | " | 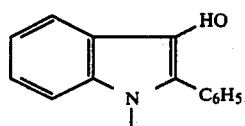 | bluish green |
| 20 | " | 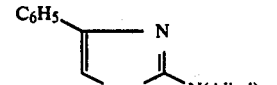 | bluish green |
| 21 | " | 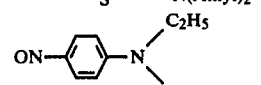 | green |
| 22 | " | 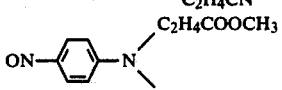 | " |
| 23 | " | 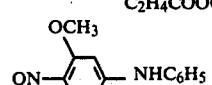 | green |
| 24 | 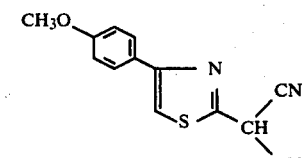 | 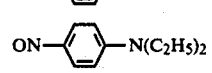 | yellowish green |
| 25 | 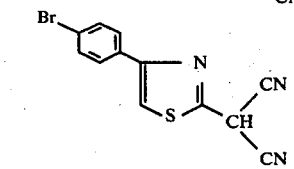 | " | yellowish green |
| 26 | 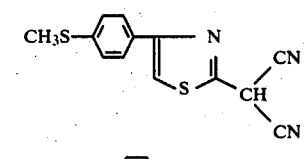 | " | yellowish green |
| 27 | 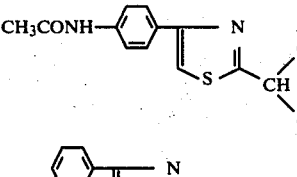 | " | yellowish green |
| 28 | 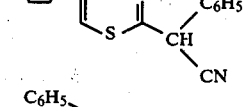 | " | violet red |
| 29 | 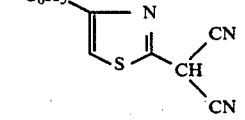 | 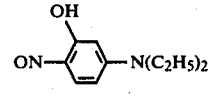 | green |

EXAMPLE 30

2 ml of phosphorous oxychloride are added to 6.4 parts of methyl 4-phenyl-thiazol-2-yl-cyanoacetate and 6.7 parts of Michler's ketone in 75 ml of chlorobenzene, and the mixture is heated at 60° C. After 3 hours it is poured onto ice and the organic phase is separated off, dried and concentrated.

Yield: 9 parts. Melting point: 98° C.

EXAMPLE 31

11.6 parts of 4-phenyl-thiazol-2-yl-malodinitrile, 16 parts of 3-methoxy-4-nitroso-diphenylamine and 1 drop of piperidine are refluxed in alcohol for 1 hour. After cooling, the dye is filtered off.

Yield: 18 parts of needles having a metallic sheen.

EXAMPLE 32

15 parts of 4-phenyl-thiazol-2-yl-cyanoacet-n-butylamide and 13 parts of 4-nitroso-cyanoethyl-ethylaniline hydrochloride in 100 parts of alcohol are boiled for 2 hours, after which the mixture is cooled and the dye is filtered off.

Yield: 13 parts of deep blue needles.

The compounds of Examples 33–81 were prepared by methods similar to that described in Example 32.

| Example | Thiazole component | Carbonyl or nitroso compound | Hue on polyester |
|---|---|---|---|
| 33 | $C_6H_5$-thiazole-CH(CN)-CONHC$_4$H$_9$ | 4-ON-C$_6$H$_3$(CH$_3$)-N(C$_2$H$_5$)(C$_2$H$_4$CN) | blue |
| 34 | " | 4-ON-C$_6$H$_3$(NHCOCH$_3$)-N(C$_2$H$_5$)$_2$ | green |
| 35 | $C_6H_5$-thiazole-CH(CN)-CON(CH$_3$)$_2$ | 4-ON-C$_6$H$_4$-N(C$_2$H$_5$)(C$_2$H$_4$CN) | bluish green |
| 36 | " | 4-ON-C$_6$H$_3$(NHCOCH$_3$)-N(C$_2$H$_5$)$_2$ | green |
| 37 | $C_6H_5$-thiazole-CH(CN)-COOC$_4$H$_9$ | 4-ON-C$_6$H$_4$-N(C$_2$H$_5$)(C$_2$H$_4$CN) | bluish green |
| 38 | $C_6H_5$-thiazole-CH(CN)-COOC$_2$H$_4$OCH$_3$ | 4-ON-C$_6$H$_4$-N(C$_2$H$_5$)$_2$ | green |
| 39 | " | 4-ON-C$_6$H$_4$-N(C$_2$H$_5$)(C$_2$H$_4$CN) | bluish green |
| 40 | $C_6H_5$-thiazole-CH(CN)-COCH$_3$ | 4-OCH-C$_6$H$_4$-N(C$_2$H$_5$)(C$_2$H$_4$CN) | blue |
| 41 | " | 4-OCH-C$_6$H$_4$-N(CH$_3$)$_2$ | bluish green |
| 42 | " | 4-ON-C$_6$H$_4$-N(C$_2$H$_5$)(C$_2$H$_4$CN) | green |
| 43 | $C_6H_5$-thiazole-CH(CN)-COC$_6$H$_5$ | 4-ON-C$_6$H$_4$-N(C$_2$H$_5$)$_2$ | green |
| 44 | $CH_3$-thiazole-CH(CN)-CN | 4-ON-C$_6$H$_4$-N(C$_2$H$_5$)$_2$ | violet |

-continued
| Example | Thiazole component | Carbonyl or nitroso compound | Hue on polyester |
|---|---|---|---|
| 45 | " | 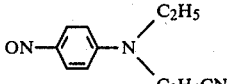 | violet |
| 46 | 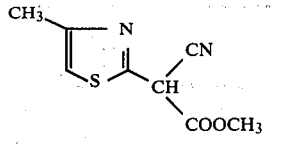 | 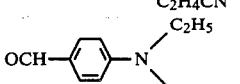 | violet red |
| 47 | 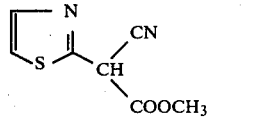 | 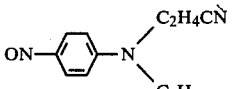 | reddish violet |
| 48 | 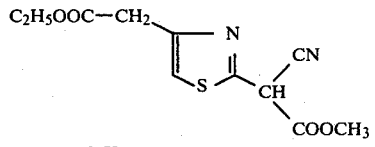 | 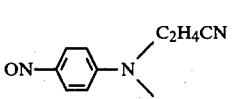 | reddish violet |
| 49[1] | 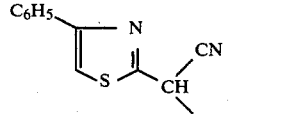 | 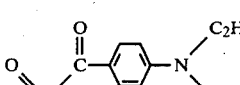 | bluish green |
| 50[1] | " | 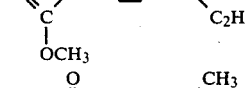 | bluish green |
| 51 | 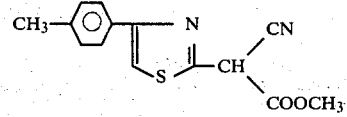 | 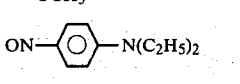 | green |
| 52 | 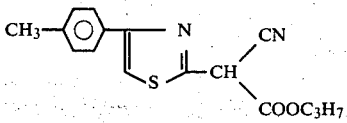 | " | " |
| 53 | 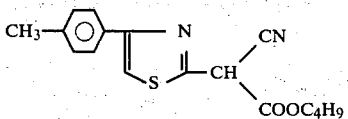 | " | " |
| 54 | 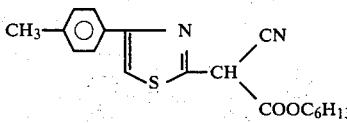 | " | " |
| 55 | 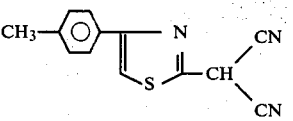 | " | " |
| 56 | 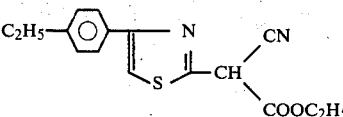 | " | " |
| 57 | 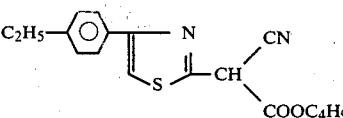 | " | " |

| Example | Thiazole component | Carbonyl or nitroso compound | Hue on polyester |
|---|---|---|---|
| 58 | 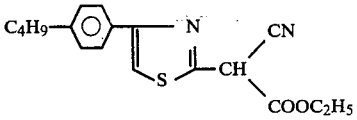 | " | " |
| 59 | 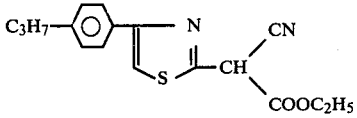 | " | " |
| 60 | 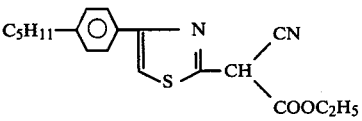 | " | " |
| 61 | 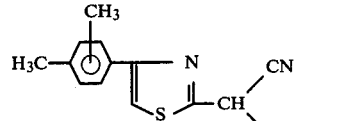 | " | " |
| 62 | 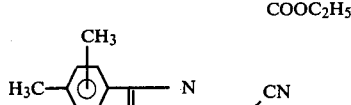 | " | " |
| 63 | 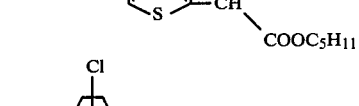 | " | " |
| 64 | 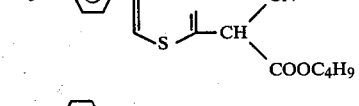 | " | " |
| 65 | 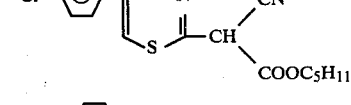 | " | " |
| 66 | 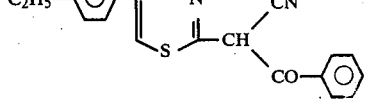 | " | " |
| 67 | 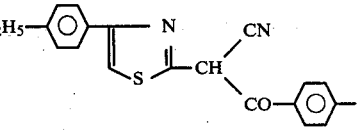 | " | " |
| 69 | 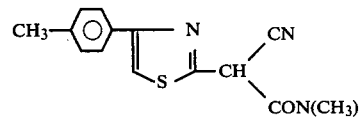 | " | " |
| 69 | 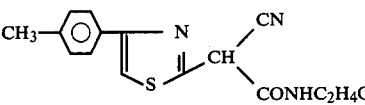 | " | " |

-continued
| Example | Thiazole component | Carbonyl or nitroso compound | Hue on polyester |
|---|---|---|---|
| 70 | 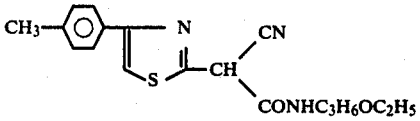 | " | " |
| 71 | 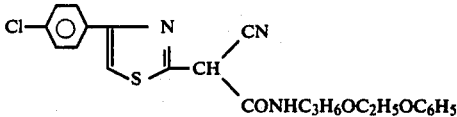 | " | " |
| 72 | 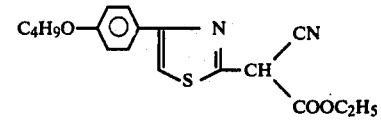 | $(C_2H_5)N\text{—}\bigcirc\text{—}NO$ | olive |
| 73 | 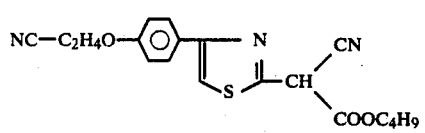 | " | olive |
| 74 | 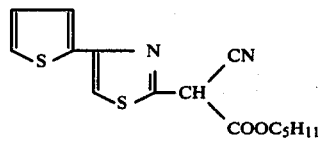 | " | olive |
| 75 | 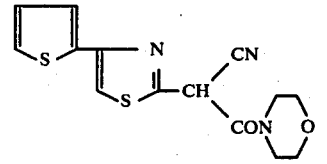 | " | green |
| 76 | 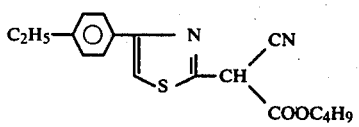 | $(Allyl)_2N\text{—}\bigcirc\text{—}NO$ | green |
| 77 | 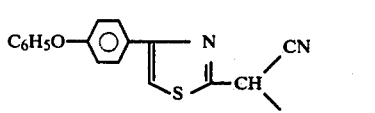 | $(CH_3)_2N\text{—}\bigcirc\text{—}NO$ | green |
| 78 | 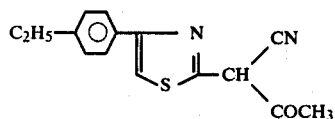 | " | green |
| 79 | 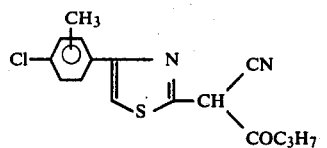 | $(C_2H_5)_2N\text{—}\bigcirc\text{—}NO$ | green |
| 80 | 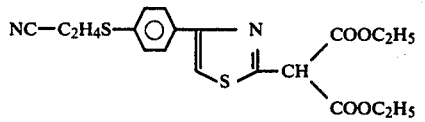 | " | green |

-continued

| Example | Thiazole component | Carbonyl or nitroso compound | Hue on polyester |
|---|---|---|---|
| 81 | CH$_3$—⟨O⟩—[thiazole]—CH(COOC$_2$H$_5$)$_2$ | (C$_2$H$_5$)$_2$N—⟨O⟩—NO | green |

[1] in boiling DMF

We claim:

1. A compound of the formula

[structure with B$^3$, B$^4$—N=, N, S, B$^1$, B$^2$]

where

B$^1$ and B$^2$ are cyano, alkanoyl of 1 to 4 carbon atoms, benzoyl which is unsubstituted or substituted by alkyl of 1 to 4 carbon atoms or by alkoxy of 1 to 4 carbon atoms, COOB$^5$ or $$CON\begin{matrix}B^6\\B^7\end{matrix},$$

B$^3$ is phenyl which is unsubstituted or is monosubstituted or polysubstituted by chlorine, bromine, alkoxy of 1 to 8 carbon atoms, alkyl of 1 to 8 carbon atoms, phenoxy, alkylmercapto of 1 to 4 carbon atoms, phenylmercapto, β-cyanoethoxy, β-C$_1$- to C$_4$-alkoxycarbonyl-ethoxy or β-cyanoethylthio, or is thienyl, B$^4$ is a radical of the formula

[two structures: aminophenyl with R$^7$, R$^8$, R$^6$ substituents, or aminonaphthyl with R$^7$, R$^8$]

B$^5$ is alkyl of 1 to 8 carbon atoms, or is alkyl of 2 or 3 carbon atoms substituted by alkoxy of 1 to 8 carbon atoms, chlorine, bromine, phenyl or C$_1$ to C$_4$-alkoxyethoxy, B$^6$ and B$^7$ independently of one another are hydrogen, alkyl of 1 to 8 carbon atoms or alkyl of 2 or 3 carbon atoms which is substituted by alkoxy of 1 to 4 carbon atoms, C$_1$- to C$_4$-alkoxyethoxy, phenoxyethoxy, cyano, C$_1$ to C$_4$-alkoxycarbonyl, alkanoyloxy of 1 to 4 carbon atoms or phenyl, or are cyclohexyl or phenyl, B$^6$ and B$^7$ together with the nitrogen may also be pyrrolidino, piperidino or morpholino, R$^6$ is hydrogen, chlorine, bromine, methyl, hydroxyl, alkoxy of 1 to 4 carbon atoms, alkanoylamino of 1 to 4 carbon atoms or benzoylamino, R$^7$ and R$^8$ independently of one another are hydrogen or alkyl of 1 to 5 carbon atoms which is unsubstituted or substituted by hydroxyl, chlorine, cyano, alkoxy of 1 to 4 carbon atoms, alkanoyloxy of 1 to 4 carbon atoms or C$_1$- to C$_4$-alkoxycarbonyl, or are allyl, cyclohexyl, benzyl, phenylethyl or phenyl.

2. The compound as claimed in claim 1, where

B$^1$ and B$^2$ are cyano, COOB$^5$ or $$CON\begin{matrix}B^6\\B^7\end{matrix},$$

B$^3$ is phenyl which is unsubstituted or is mono-substituted or polysubstituted by chlorine, alkoxy of 1 to 5 carbon atoms, alkyl of 1 to 5 carbon atoms or β-cyanoethoxy, B$^4$ is a radical of the formula

[aminophenyl structure with R$^7$, R$^8$, R$^6$] and

B$^5$, B$^6$, B$^7$, R$^6$, R$^7$ and R$^8$ have the above meanings.

3. The compound as claimed in claim 2, where

B$^5$ is alkyl of 1 to 4 carbon atoms, or is alkyl of 2 or 3 carbon atoms substituted by alkoxy of 1 to 4 carbon atoms, B$^6$ and B$^7$ independently of one another are hydrogen, alkyl of 1 to 4 carbon atoms or alkyl of 2 or 3 carbon atoms which is substituted by alkoxy of 1 to 4 carbon atoms, C$_1$- to C$_4$-alkoxyethoxy or phenoxyethoxy, or are phenyl, and the remaining substituents have the above meanings.

4. The compound as claimed in claim 2, where

R$^6$ is hydrogen, chlorine, methyl, methoxy or acetylamino,

R$^7$ and R$^8$ independently of one another are alkyl of 1 to 5 carbon atoms or alkyl of 2 or 3 carbon atoms which is substituted by hydroxyl, cyano, alkoxy of 1 to 4 carbon atoms, alkanoyloxy of 1 to 4 carbon atoms or C$_1$- to C$_4$-alkoxycarbonyl, or are allyl or phenylethyl and the remaining substituents have the above meanings.

5. The compound as claimed in claim 2 of the formula

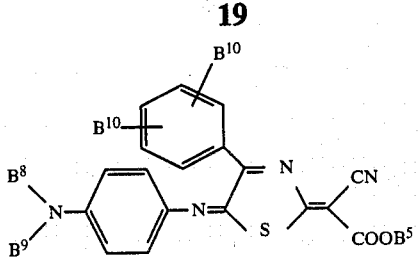
where
$B^8$ and $B^9$ independently of one another are alkyl of 1 to 4 carbon atoms,
$B^{10}$ is hydrogen, alkyl of 1 to 5 carbon atoms or chlorine and
$B^5$ has the above meaning.
* * * * *